United States Patent [19]

Sugioka et al.

[11] Patent Number: 5,428,181

[45] Date of Patent: Jun. 27, 1995

[54] BISPHOSPHONATE DERIVATIVE

[75] Inventors: Tatsuo Sugioka, Iruma; Mizuho Inazu, Saitama, both of Japan

[73] Assignee: Hoechst Japan Limited, Tokyo, Japan

[21] Appl. No.: 996,596

[22] Filed: Dec. 24, 1992

[30] Foreign Application Priority Data

Dec. 26, 1991 [JP] Japan .................. 3-344253
Nov. 20, 1992 [JP] Japan .................. 4-311876

[51] Int. Cl.$^6$ .............................................. C07J 1/00
[52] U.S. Cl. .................... 552/506; 552/507; 540/5; 549/220; 562/21; 558/161
[58] Field of Search .............. 540/5; 552/506, 507; 549/220; 562/21; 558/161

[56] References Cited

U.S. PATENT DOCUMENTS

| 4,732,998 | 3/1988 | Binderup et al. | 558/161 |
| 5,130,304 | 7/1992 | Binderup et al. | 514/91 |
| 5,183,815 | 2/1993 | Sarri et al. | 514/172 |

FOREIGN PATENT DOCUMENTS

| 0185589 | 6/1986 | European Pat. Off. |
| 0341961 | 11/1989 | European Pat. Off. |
| 0350002 | 1/1990 | |
| WO86/00902 | 2/1986 | WIPO |

OTHER PUBLICATIONS

J. Kulagowski et al.; "Inhibitors of myo–Inositol Monophosphatase Containing Methylenebisphosphonic Acid as a Replacement for a Phosphate Group", J. Chem. Coc. Chem Commun.; pp. 1649–1651 (1991).

D. Pert et al.; "An alternative Route to 2–Bromo–and 2–Iodo–estradiols from Estradiol"; Aust. J. Chem.; 40:303–309 (1986).

H. Fleisch, "Bisphosphonates–History and Experimental Basis"; Pergamon Journals Ltd.; pp. S23–S26 (1987).

M. Regitz et al.; "Syntheses von Alpha–Diazo–Phosphonsäureestern", Chem. Ber.; 101:3374–3734 (1968).

J. Walmsley et al.; "The Donor Properties of Bis–(diisopropoxyphosphinyl)–methane and Bis–(di–N–butyl-phosphinyl)–methane"; Inorganic Chemistry; pp. 312–318 (1962).

Fujisaki et al., Chemical Abstracts, vol. 114, No. 9, p. 766; column 2, abstract No. 82119 (Mar. 4, 1991).

Fujisaki et al., Chemical Abstracts, vol. 115, No. 5, p. 877; column 2, abstract No. 49974 (Aug. 5, 1991).

Primary Examiner—Johann Richter
Assistant Examiner—Kimberly J. Kestler
Attorney, Agent, or Firm—Finnegan, Henderson, Farabow, Garrett & Dunner

[57] ABSTRACT

A compound represented by the general formula:

$$\left[ A-O-X-C \begin{matrix} H \\ \diagup \\ \diagdown \end{matrix} \begin{matrix} P(OR_1)_2 \\ \| \\ O \\ P(OR_1)_2 \\ \| \\ O \end{matrix} \right]_q \quad (1)$$

wherein A–O–denotes a residue of a compound having an estrogenic activity; $R_1$ denotes H or a $C_1$–$C_6$ alkyl group; X denotes a single bond, a $C_1$–$C_{10}$ alkylene group or a group of the formula

[structures shown: $-(CH_2)_n-$ cycloalkyl with $R_2$; $-(CH_2)_k-$phenyl$-(CH_2)_L-$ with Z; or $-(CH_2)_k-$pyridyl$-(CH_2)_L-$ with Z]

wherein $R_2$ denotes H or a $C_1$–$C_5$ alkyl group; Z denotes a nitro group or a halogen; n is an integer of 3 to 12; k is an integer of 1 to 5; L is an integer of 0 to 5; and q is an integer of 1 to 3, and physiologically acceptable salts thereof are disclosed.

The compounds have a high affinity to bone tissues, and the compounds per se and metabolites thereof show significant therapeutic effect on bone diseases such as osteoporosis, rheumatoid arthritis and osteoarthritis.

9 Claims, No Drawings

BISPHOSPHONATE DERIVATIVE

FIELD OF THE INVENTION

This invention relates to bisphosphonate derivatives derived from a natural or synthetic compound having a hormonal activity as estrogen, more particularly to bisphosphonate derivatives in which a natural or synthetic compound having a hydroxyl group in the molecule and possessing a hormonal activity as estrogen is coupled directly or through an appropriate spacer with a bisphosphonate derivative. These bisphosphonate derivatives are useful as therapeutic agents for bone diseases such as osteoporosis, rheumatoid arthritis and osteoarthritis.

Therapeutic agents for bone diseases such as estrogen, calcitonins, vitamin $D_3$ and derivatives thereof, ipriflavone and bisphosphonate derivatives are currently available. While estrogen is therapeutically useful in bone diseases, there are pointed out risks of causing intrauterine hemorrhage and more or less increasing development of endometrial cancer and breast cancer ("IGAKUNOAYUMI (Development of Medical Science)", p. 749, vol. 152, No. 12, 1990). It is, therefore, desirable to selectively deliver estrogen to the affected part of bone thereby reducing the possible adverse reactions. Additionally, estrogen has a side effect increasing uterine weights. On the other hand, bisphosphonate derivatives, known bone resorption inhibitors, which have a high affinity to bone tissues and are hardly metabolized, are also reported for their possible uses as a drug carrier (Bone, vol. 8, suppl., 1, S23-S28, 1987).

The present inventors made intensive studies with a view to enhancing the pharmacological activities of estrogen and bisphosphonate derivatives which are known to be therapeutic agents for bone diseases as well as reducing their side effects, and they were successful in synthesizing novel compounds in which estrogen having a hydroxyl group in the molecule is coupled either directly or through a variety of spacers with a bisphosphonate derivative. The novel compounds when administered to living bodies are selectively transferred to bone tissues and the compounds per se or their metabolites exhibit significant therapeutic effects on bone diseases such as osteoporosis, rheumatoid arthritis and osteoarthritis, but no side effect increasing uterine weights.

The compounds of this invention are novel and include those represented by the general formula (I),

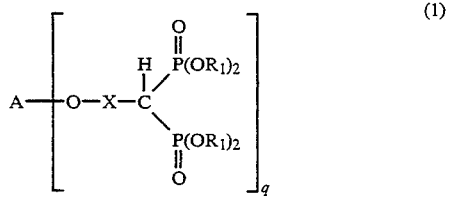

(1)

wherein A-O- denotes a residue of a compound having an estrogenic activity; $R_1$ denotes H or a $C_1$-$C_6$ alkyl group; X denotes a single bond, a $C_1$-$C_{10}$ alkylene group or a group of the formula:

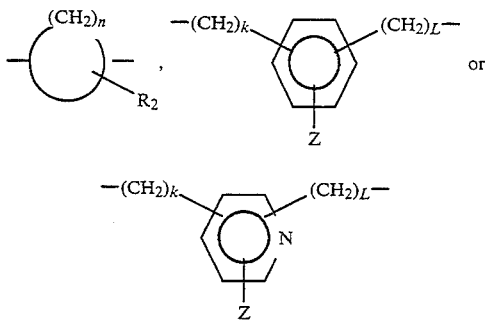

wherein $R_2$ denotes H or a $C_1$-$C_5$ alkyl group; Z denotes a nitro group or a halogen; n is an integer of 3 to 12; k is an integer of 1 to 5; L is an integer of 0 to 5; and q is an integer of 1 to 3, and physiologically acceptable salts thereof. The residue A-O- is a group which is obtained by removing a hydrogen atom(s) from a hydroxyl group(s) of a compound possessing an estrogenic activity. The compound possessing an estrogenic activity includes those having a hydroxyl group in the molecule and possessing an estrogenic activity, for example, natural estrogen such as estron, estradiol and estriol or derivatives thereof; plant estrogen including isoflavon derivatives known to be nonsteroid estrogen such as genistein, biochanin-A, formononetin and daidzein, flavon derivatives such as coumestrol, and miroestrol; as well as synthetic estrogen such as stilbestrol, hexestrol and benzestrol or derivatives thereof. The $C_1$-$C_6$ alkyl group for $R_1$ may be straight or branched and includes methyl, ethyl, propyl, isopropyl, n-butyl, sec-butyl, isobutyl, tert-butyl, n-pentyl, neopentyl and n-hexyl. The $C_1$-$C_{10}$ alkylene group for X may also be straight or branched and includes methylene, ethylene, trimethylene, n-butylene, isobutylene, tert-butylene, n-pentylene, neopentylene, n-hexylene, n-heptylene, n-octylene, n-nonylene, n-decalene. The halogen for Z includes fluorine, chlorine, bromine and iodine. The desired compound [I] and its physiologically acceptable salts according to this invention can be prepared, for example, in the following manners, depending on the kind of spacer for coupling the compound having an estrogenic activity with the bisphosphonate derivative:

Method 1

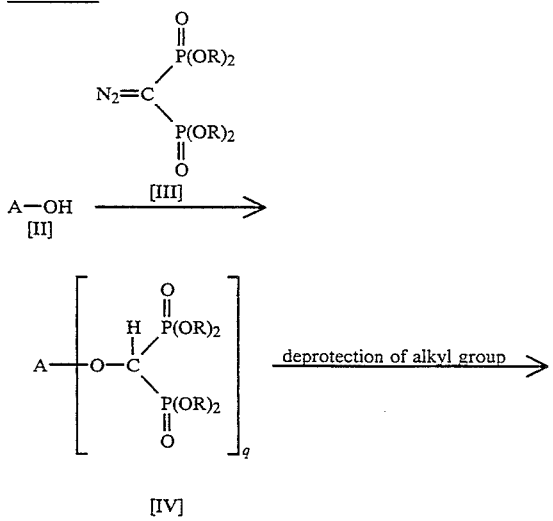

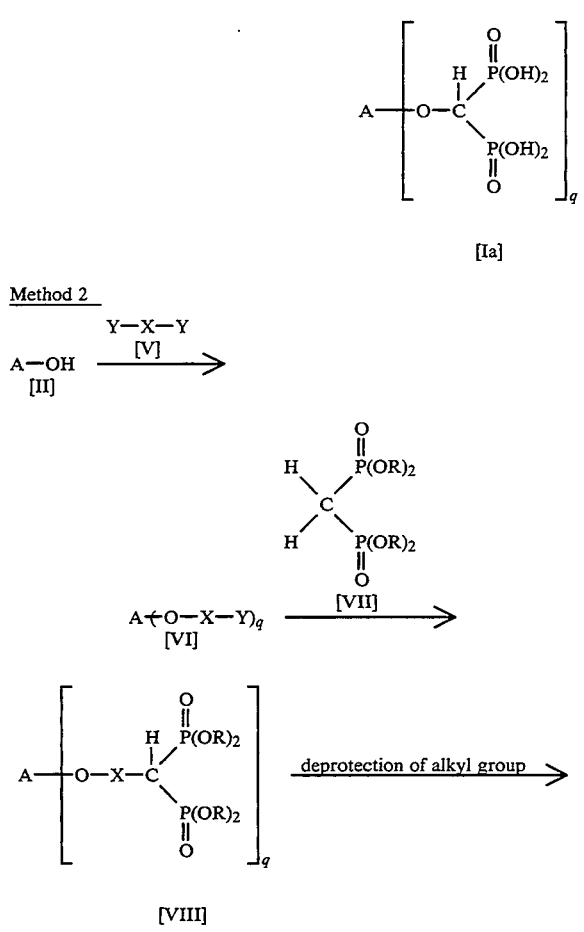

wherein A-O-, R and X have the same meanings as defined above; R denotes a $C_1$–$C_6$ alkyl group; and Y denotes a group to be eliminated such as a halogen atom and a tosyl group.

The starting materials [II] and [VII] can be synthesized according to the known method disclosed in Chem. Ber., vol. 101, p.3734 (1968) or Inorg. Chem. Vol. 2, p.312 (1963). The above definitions will be described below more specifically.

The protected hydroxyl group (OR) can be exemplified by lower alkoxy groups such as methoxy, ethoxy, propoxy, isopropoxy, butoxy, sec-butoxy, isobutoxy, tert-butoxy, pentyloxy, neopentyloxy and hexyloxy, more preferably $C_1$–$C_4$ alkoxy groups. The group to be released (Y) can be exemplified by halogen atoms such as chlorine, bromine and iodine, as well as tosyl group. The physiologically acceptable salts of the compound [I] can be exemplified by metal salts such as sodium salts, potassium salts, calcium salts and magnesium salts, as well as organic amine salts such as ammonium salts, trimethylamine salts, triethylamine salts and dicyclohexylamine salts.

Process for preparing the desired compounds [I] and salts thereof will be described below more specifically.

METHOD 1

The desired compound [Ia] and the salts thereof can be obtained by deprotection of the hydroxyl protective group from the compound [IV] prepared by allowing the compound [II] having an estrogenic activity to react with a compound [III]. While the reaction for obtaining the compound [IV] by reacting the compound [II] having an estrogenic activity with the compound [III] is usually carried out in a solvent such as benzene, toluene, xylene, chlorobenzene, di-n-butyl ether, dioxane, dimethyl-formamide and dimethyl sulfoxide, the reaction can be carried out in any other organic solvents which do not affect the reaction. The reaction is carried out with light irradiation or heating. When the reaction is effected with heating, a copper or silver salt of active methylene compounds such as acetylacetone, or a rhodium salt of acetic acid can effectively be used as a catalyst. While the reaction temperature is not critical, the reaction is usually carried out at room temperature or with heating. The reaction for deprotecting the hydroxyl protective group of the compound [IV] to give the desired compound [Ia] or salt thereof is carried out by the conventional procedure such as hydrolysis and reduction.

The hydrolysis is preferably carried out in the presence of a base, an acid including Lewis acids or a halosilane compound. The base can be exemplified by inorganic bases such as alkali metal hydroxides (e.g. sodium hydroxide, potassium hydroxide etc.), alkali metal carbonates (e.g. sodium carbonate, potassium carbonate etc.) or organic bases such as triethylamine or pyridine. The acid can be exemplified by organic acids such as formic acid, acetic acid, propionic acid, trichloroacetic acid and trifluoroacetic acid, as well as inorganic acids such as hydrochloric acid, hydrobromic acid, sulfuric acid, hydrogen chloride and hydrogen bromide.

The halosilane compound can be exemplified by halo-tri-(lower)-alkylsilanes such as iodotrimethylsilane and bromotrimethylsilane. Incidentally, when a Lewis acid such as trihaloacetic acids, e.g, trichloroacetic acid and trifluoroacetic acid, is used in the deprotection reaction, the reaction is preferably carried out in the presence of a cation scavenger such as anisole and phenol.

While the reaction is usually carried out in water, an alcohol such as methanol and ethanol, methylene chloride, acetonitrile, chloroform, tetrachloromethane, tetrahydrofuran or a mixture of these solvents, the reaction can be carried out in any other solvents which do not affect the reaction. Incidentally, a liquid base, acid or halosilane compound can be used as the solvent.

While the reaction temperature is not critical, the reaction is usually carried out with cooling or heating.

Meanwhile, the reduction to be applied to the deprotection for the hydroxyl protective group includes chemical reduction and catalytic reduction.

Reducing agents to be suitably employed for the chemical reduction can be exemplified by a combination of a metal such as tin, zinc and iron or a metal compound such as chromium chloride and chromium acetate with an organic or inorganic acid such as formic acid, acetic acid, propionic acid, trifluoroacetic acid, potoluenesulfonic acid, hydrochloric acid and hydrobromic acid.

Catalysts to be suitably used for the catalytic reduction include, for example, platinum catalysts such as platinum plate, platinum sponge, platinum black, colloidal platinum, platinum oxide and platinum wire; palladium catalysts such as palladium sponge, palladium black, palladium oxide, palladium-carbon, colloidal palladium, palladium-barium sulfate and palladium-barium carbonate; nickel catalysts such as reduced nickel, nickel oxide and Raney nickel; cobalt catalysts such as reduced cobalt and Raney cobalt; iron catalysts such as reduced iron and Raney iron; and copper catalysts such as reduced copper, Raney copper and Ullman-copper, which are conventionally used.

The deprotection reaction resorting to the chemical reduction is usually carried out in a conventional solvent which does not affect the reaction such as water, methanol, ethanol, propanol and N,N-dimethylformamide or a mixture of these solvents. Incidentally, when a liquid form acid is used for the chemical reduction, it is also possible to allow the acid to serve as the solvent.

As the solvent to be used for the catalytic reduction, conventional solvents such as diethyl ether, dioxane and tetrahydrofuran or a mixture thereof can also be used in addition to those described above.

The temperature for these reactions are not critical, and the reactions are carried out with cooling or heating.

METHOD 2

The desired compound [Ib] or salt thereof can be synthesized as follows: A compound [II] having an estrogenic activity is reacted with a compound [V] to synthesize a compound [VI]. The compound [VI] is reacted with a bisphosphonate derivative [VII] to give a compound [VIII], which is then subjected to the hydroxyl protective group elimination reaction to give the desired compound [Ib] or salt thereof.

While the reaction for obtaining a compound [VI] by reacting a compound [II] having an estrogenic activity with a compound [V] is usually carried out in a solvent such as acetone, tetrahydrofuran, diethyl ether, dioxane, toluene, dimethylformamide and dimethyl sulfoxide, it can also be carried out in any other solvents which do not affect the reaction. The reaction temperature is not critical, and the reaction is usually carried out with cooling or heating. Incidentally, the reaction is carried out in the presence of a binding agent such as an inorganic or organic base, for example, an alkali metal hydride such as sodium hydride and potassium hydride; an alkaline earth metal hydride such as calcium hydride and magnesium hydride; an alkali metal hydroxide such as sodium hydroxide and potassium hydroxide; an alkali metal carbonate such as sodium carbonate and potassium carbonate; an alkali metal hydrogencarbonate such as sodium hydrogencarbonate and potassium hydrogencarbonate; an alkali metal fluoride such as sodium fluoride, potassium fluoride and cesium fluoride; an alkali metal alkoxide such as sodium methoxide, sodium ethoxide and potassium tert-butoxide; a trialkylamine such as trimethylamine and triethylamine; picoline, 1,5-diaza-bicyclo[4,3,0]non-5-en, 1,4-diazabicyclo[2,2,-21octane and 1,5-diazabicyclo[5,4,0]undecene-5.

The reaction for obtaining a compound [VIII] by reacting a compound [VI] with a bisphosphonate derivative [VII] can be carried out in the same manner as in the synthesis of the compound [VI]. The reaction for obtaining the desired compound [Ib] or salt thereof by deprotecting the hydroxyl protective group of the compound [VIII] can be carried out in the same manner as described in Method 1.

The process for preparing the compound [I] or salt thereof may not be limited to the above methods, but it can be prepared according to the method, for example, described in J. Chem. Soc. Chem. Commun. p. 1649, 1991.

If the desired compound [I] has one or more stereoisomers, such as optical isomers and geometrical isomers, based on the asymmetric carbon atom or double bond present in the molecule, such isomers and mixtures thereof are all included within the scope of the desired compound [I].

If the compound [II] possessing an estrogenic activity has a plurality of hydroxyl groups, the binding site with the bisphosphonate derivative may not particularly be limited, and those compounds in which all or a particular hydroxyl group is bound with the bisphosphonate derivative are also included within the scope of the desired compound [I].

If the compound possessing an estrogenic activity and having a plurality of hydroxyl groups and reactive functional groups such as amine, carboxylic acid and ketone is allowed to react at a particular hydroxyl group with the bisphosphonate derivative, the hydroxyl group or the reactive functional group other than the particular hydroxy group to be reacted is protected with suitable protective groups, followed by deprotection, to obtain the desired compound [I].

Typical examples of the compound of the invention are listed below.

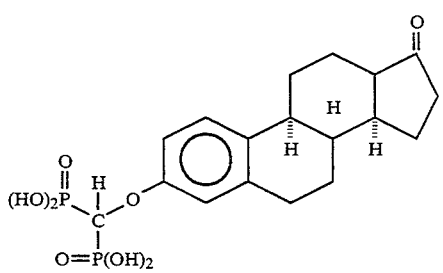

[XI]

-continued
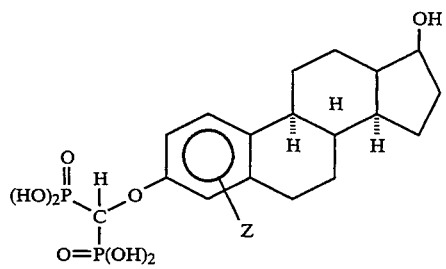
[XII]
z = H, NO₂, halogen
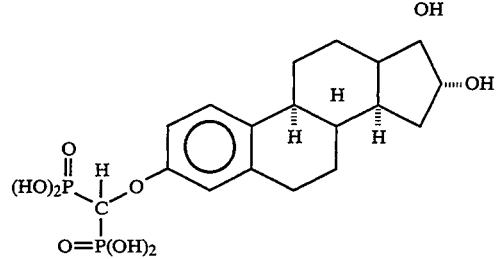
[XIII]
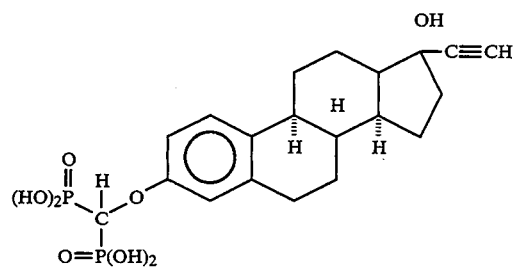
[XIV]
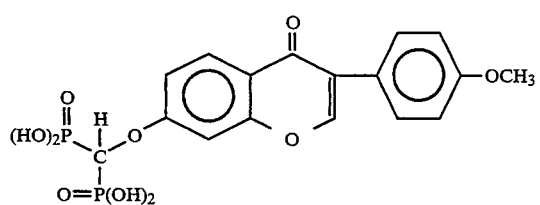
[XV]
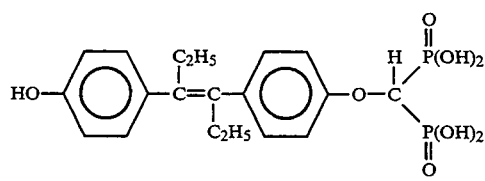
[XVI]
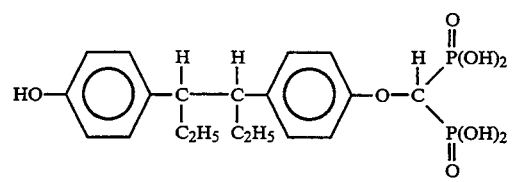
[XVII]
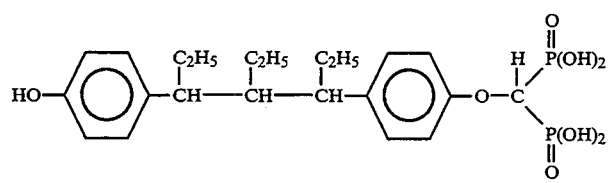
[XVIII]

-continued
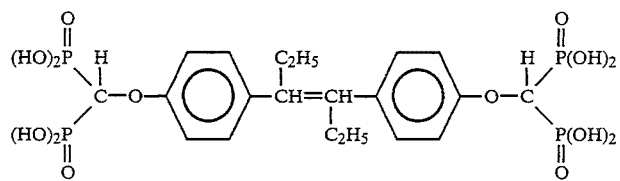 [XIX]
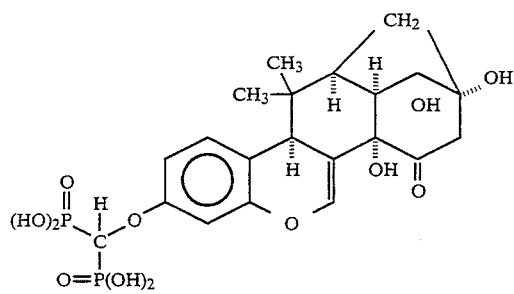 [XX]
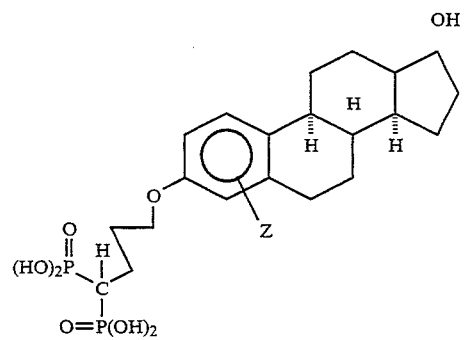 [XXI]
z = H, NO₂, halogen
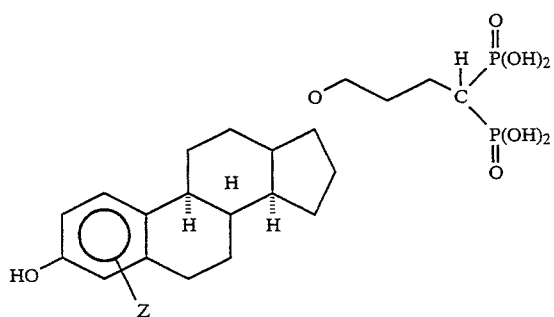 [XXII]
z = H, NO₂, halogen
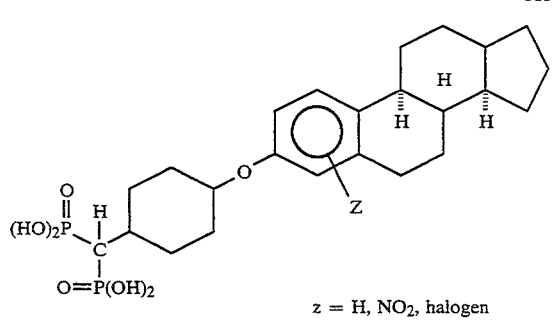 [XXIII]
z = H, NO₂, halogen

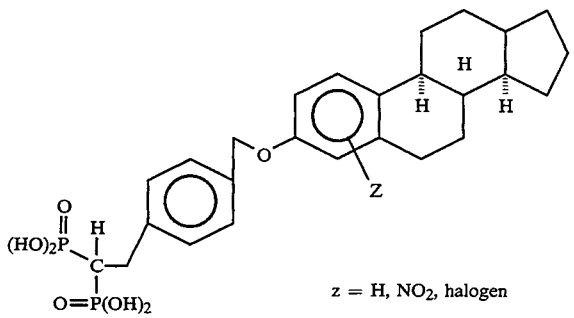

z = H, NO₂, halogen

The invention also relates to a pharmaceutical composition for treating bone diseases comprising an effective amount of the compound of the formula I or physiologically acceptable salt thereof in combination with a pharmaceutically acceptable carrier or excipient.

The invention further relates to the use of an effective amount of a compound of the formula I for the preparation of a pharmaceutical composition for the treatment of bone diseases.

The compound of the invention can usually be administered to an adult at a unit dose of 1 00 μg to 1,000 mg, preferably 200 μg to 200 mg once per 1 to 15 days orally or parenterally such as by intravenous injection, subcutaneous injection and intramuscular injection. The dosage may suitably be adjusted depending on the kind of the compound, age and sex of the patient, administration route, body weight and condition.

The compound of the invention is allowed to have a dosage form for oral or parenteral administration using, as necessary, a pharmaceutical carrier or excipient.

Tablets, powders, capsules and granules for oral administration may contain a conventional adjuvant; that is an excipient, a binder, a disintegrator and a lubricant such as crystalline cellulose, calcium carbonate, calcium phosphate, corn starch, potato starch, sugar, lactose, talc, magnesium stearate and gum arabic. Liquid preparations for oral administration may be in the form of aqueous or oily suspension, solution, syrup, elixir, etc.

Injections may be in the form of solution or suspension and contain a prescribed agent such as a suspending agent, a stabilizer and a dispersant and further a sterile distilled water, a purified oil such as peanut oil and corn oil, a nonaqueous solvent, polyethylene glycol or polypropylene glycol.

The compound of the invention will be described below specifically by way of Examples.

EXAMPLE 1

The starting material 17-(methoxymethoxy)-estra-1,3,5(10)- trien-3-ol can be prepared according to the method described in Aust. J. Chem., vol. 40, No. 2, pp. 303-309 (1987).

(i) To a solution of 17-(methoxymethoxy)-estra-1,3,5-(10)-trien-3-ol (3.0 g)in toluene (30 ml) is added copper (II) salt of acetylacetone (0.1 g), and the resulting mixture is heated under reflux. To the resulting solution is dropwise added a solution of tetra-isopropyl (diazomethylene)bis(phosphonate) (4.2 g) in toluene (10 ml) over about one hour. After completion of the addition, the mixture is stirred for additional one hour and then cooled. The reaction solution is treated with a small amount of active carbon and then concentrated under reduced pressure. The residue thus obtained is purified over column chromatography (ethyl acetate:-chloroform:methanol=70:30:2) to give 3-[(bisphosphono-methyl)oxy]-17-(methoxymethoxy)-estra-1,3,5(10)-triene tetraisopropyl ester (2.85 g).

MS(DI-EI) m/z 658 (M+), 614, 596, 473, 409, 329
¹HNMR (89.55 MHz, CDCl₃) δ 0.81 (3H, s), 1.3 (24H, t-like), 1.2–2.4 (13H, m), 2.80 (2H, m), 3.4 (3H, s), 3.61 (1H, t, J=7.7 Hz), 4.66 (2H, s), 4.71 (1H, t, J=17.4 Hz), 4.6–5.1 (4H, m), 6.79 (1H, s), 6.83 (1H, d, J=7.2 Hz), 7.17 (1H, d, J=7.2 Hz)

(ii) To a solution of the compound (1.1 g) obtained above under (i) in dry chloroform (20 ml) is added bromo-trimethylsilane (1.54 g) at 0° C., and the resulting mixture is stirred at 0° C. for one hour and then at room temperature for 24 hours. To the reaction mixture cooled to 0° C. is added water (2 ml), followed by stirring for 30 minutes. The solvent is removed under reduced pressure, and the residue is crystallized from an ethanol-acetone system to give 3-[(bis-phosphonomethyl)oxy]-estra- 1,3,5( 10)-trien-17-ol [IX] (0.51 g) having the structural formula:

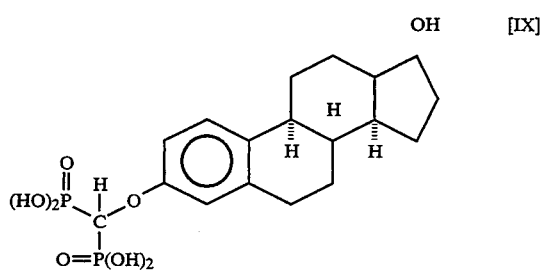

MS (FAB)m/z 447 (M++1), 539 (M++G+1)
¹HNMR (500.2 MHz, DMSO-d6) δ 0.668 (3H, s), 1.04–1.44 (7H, m), 1.582 (1H, m), 1.75–1.95 (3H, m), 2.10 (1H, m), 2.269 (1H, d-like, J=10.8 Hz), 2.753 (2H, brs), 3.523 (1H, t-like, J=8.3 Hz), 4.529 (1H, t, J=17.1 Hz), 5.48 (brs, OH), 6.743 (1H, d, J=2 Hz), 6.803 (1H, dd, J=8.8, 2 Hz), 7.15 (1H, d, J=8.8 Hz)

¹³CNMR (125.8 MHz, DMSO-d6) δ 11.153, 22.679, 25.945, 26.770, 29.181, 29.787, 36.492, 38.467, 42.713, 43.507, 49.449, 73.170 (t, J=149.7 Hz), 79.936, 113,566, 115.774, 125.807, 133.025, 137.007, 157.088

EXAMPLE 2

(i) A suspension of a 60 % sodium hydride (0.531 g) in tetrahydrofuran (100 ml) is cooled to 0° C., and 17-(methoxymethoxy)-estra-1,3,5(10)-trien-3-ol (3.5 g) is slowly added thereto. After addition of dimethylformamide (50 ml), the mixture is stirred at room temperature for 2 hours. To the resulting solution is added 1,3-dibromo-propane (2.68 g), and the mixture is stirred at room temperature overnight. The reaction mixture is poured into an aqueous ammonium chloride, followed by extraction with ethyl acetate. The solvent is removed under reduced pressure and the residue thus obtained is purified over column chromatography (n-hexane:ethyl acetate=2:1) to give 3-[(3-bromopropyl)oxy]- 17-(methoxymethoxy)-estra-1,3,5(10)-triene (3.0 g).

$^1$HNMR (89.55 MHz, CDCl$_3$) δ 0.81 (3H, s), 1.1–2.5 (15H, m), 2.81 (2H, m), 3.37 (3H, s), 3.45–3.70 (3H, m), 4.08 (2H, t, J=5.6 Hz), 4.67 (2H, s), 6.65 (1 H, s), 6.69 (1H, d, J=8.2 Hz), 7.20 (1H, d, J=8.2 Hz)

(ii) A suspension of a 60 % sodium hydride (0.220 g) in toluene (20 ml) is cooled to 0° C., and a solution of tetraisopropyl methylenebisphosphonate (1.75 g) in toluene (5 ml) is added dropwise thereto. Upon ceasing of hydrogen gas generation after completion of the addition, a solution of 3-[(3-bromopropyl)oxy]- 17-(methoxymethoxy)-estra- 1,3,5-( 10)-triene (2 g) in toluene (5 ml) is added. The mixture is gradually heated to about 80° C. and stirred at this temperature for 5 hours. After completion of the reaction, the reaction mixture is poured into an aqueous ammonium chloride, followed by extraction with ethyl acetate. The solvent is removed under reduced pressure, and the residue is purified over column chromatography (chloroform:methanol=30:2) to give 3-[(4,4-bisphosphono-butyl)oxy]- 17-(methoxymethoxy)-estra-1,3,5(10-triene tetraisopropyl ester (1.15 g).

MS (DI-EI) m/z 700 (M+), 615, 515

$^1$HNMR (89.55 MHz, CDCl$_3$) δ 0.80 (3H, s), 1.33 (24H, d, J=5.9 Hz), 1.1–2.5 (18H, m), 2.80 (2H, m), 3.38 (3H, s), 3.62 (1H, t, J=7.7 Hz), 3.94 (2H, t-like), 4.67 (2H, s), 4.5–5.0 (5H, m), 6.61 (1H, s), 6.65 (1H, d, J=8 Hz), 7.18 (1H, d, J=8.4 Hz)

(iii) The compound (1.50 g) obtained above under (ii)is treated in the same manner as in Example 1 (ii) to give 3-[(4,4-bisphosphonobutyl)oxy]-estra-1,3,5(10)-trien-17-ol [X] (0.55 g).

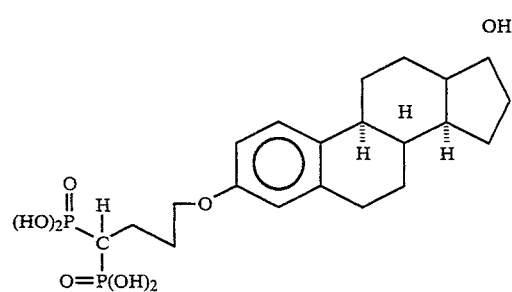

MS (FAB)m/z 489 (M+ +1)

$^1$HNMR (500.2 Mhz, DMSO-d6) δ 0.663 (3H, s), 1.0–1.44 (7H, m), 1.575 (1H, m), 1.70–2.15 (gH, m), 2.253 (1H, d-like, J=10.3 Hz), 2.752 (2H, brs), 3.519 (1H, t-like, J=8.3 Hz), 3.878 (2H, brs), 5.268 (brs, OH), 6.594 (1H, d, J=2 Hz), 6.658 (1H, dd, J=8.8, 2 Hz), 7.142 (1H, d, J=8.8 Hz)

$^{13}$CNMR (125.8 MHz, DMSO-d6) δ 11.168, 21.870, 22.694, 25.945, 26.785, 28.310 (t, J=6.9 Hz), 29.165, 29.803, 36.507, 37.736 (t, J=123.3 Hz), 38.514, 42.729, 43.445, 49.464, 67.103, 79.952, 111.886, 114.079, 126.025, 132.045, 137.302, 156.357

EXAMPLE 3

| Tablets | |
|---|---|
| Compound [IX] | 5 g |
| lactose | 25 g |
| starch | 98 g |
| carboxymethyl cellulose calcium | 20 g |
| magnesium stearate | 2 g |

According to a conventional means, said compounds are mixed, granurated and tabletted to prepare 1000 tablets containing 5 mg of Compound [IX] per tablet.

EXAMPLE 4

| Capsules | |
|---|---|
| Compound [X] | 5 g |
| lactose | 80 g |
| starch | 100 g |
| hydroxypropylcellulose | 10 g |
| magnesium stearate | 5 g |

According to a conventional means, said compounds are mixed, granurated and the mixture is filled into No. 3 capsules in an amount of 200 mg per capsule of No. 3 to prepare 1000 capsules containing 5 mg of Compound [IX] per capsule.

EXAMPLE 5

The estrogenic effects on uterine weights of Compound [IX] which was synthesized according to Example 1 and Compound [X] which was synthesized according to Example 2 were examined. Three-week-old female SD rats were divided into 7 or 8 number per group. The test compounds or estradiol suspended in olive oil were subcutaneously administered, and as a control, olive oil was administered in the same manner. Four hours later, the uterine weights were examined and evaluated among the control group and the ones tested by Student-t test. The results were shown in Table 1. The uterine weights of the group which was administered by 50 or 500 μg/kg of estradiol increased significantly as compared with those of the control group. On the contrary, the uterine weights did not increase in the groups which were administered by 100 and 1000 μg/kg of Compound [IX] and Compound [X], respectively, so as to be nearly equivalent to estradiol in mol comparison.

TABLE 1

| Test compound | Dose (μg/kg) | Uterine weight (g) |
|---|---|---|
| Control (olive oil) | 0 | 0.032 ± 0.005 |
| estradiol | 50 | 0.040 ± 0.008* |
|  | 500 | 0.053 ± 0.007** |
| Compound [IX] | 100 | 0.031 ± 0.008 |
|  | 1000 | 0.033 ± 0.004 |
| Compound [X] | 100 | 0.033 ± 0.004 |
|  | 1000 | 0.032 ± 0.003 |

Mean ± S.D.
*p < 0.05,
**p < 0.01 vs. control

EXAMPLE 6

The effects of Compound [IX] and Compound [X] on a hypercalcemic model was examined.

After twenty hours of fasting, 60 unit/kg of human parathyroid hormone (N1-34), hereinafter abbreviated to PTH, were administered intravenously to five-week-old male SD rats that had been divided into 5 number per group and prepared a hypercalcemic model. The test compounds were suspended in olive oil and subcutaneously administered three days before the injection of PTH, and as a control, olive oil was administered in the same manner. Sixty minutes after the injection of PTH, the blood was collected and the serum was separated in order to measure the serum ionized $Ca^{++}$ level. The serum $Ca^{++}$ level was evaluated among the control (PTH+) group and the group tested by Student-t test.

The results were shown in Table 2. The serum ionized $Ca^{++}$ level increased significantly by injection of PTH, which indicated that hypercalcemia was induced. The hypercalcemia was inhibited in the groups of Compound [IX] and Compound [X] by administration of 3.0 mg/kg each; in particular, the significant suppressive effect was observed in the group of Compound [X].

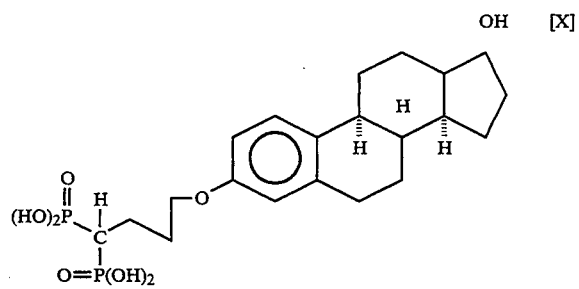

TABLE 2

| Test compound | Dose (mg/kg) | Serum $Ca^{++}$ level (m mol/l) |
|---|---|---|
| control (PTH−) | 0 | 1.31 ± 0.02** |
| control (PTH+) | 0 | 1.38 ± 0.02 |
| Compound [IX] | 0.03 | 1.38 ± 0.02 |
|  | 0.3 | 1.37 ± 0.02 |
|  | 3.0 | 1.35 ± 0.03 |
| Compound [X] | 0.03 | 1.37 ± 0.03 |
|  | 0.3 | 1.38 ± 0.03 |
|  | 3.0 | 1.34 ± 0.03* |

Mean ± S.D.
*p < 0.05,
**p < 0.01 vs. PTH+ control

EXAMPLE 7

The anti-osteoporotic effects of Compound [IX] and Compound [X] on ovariectomized mice were examined. 10-week-old ICR mice were divided into 5 number per group and were ovariectomized. Compound [IX] and Compound [X] were administered subcutaneously for consecutive six weeks after the operation. 500 μg/kg of the test compounds were suspended in olive oil, and subcutaneously administered everyday to the mice. As a control, solely olive oil was administered in the same manner. After the administration, the right femurs were taken out. Then the outer width and the cortical width of the center part of the femur shafts were measured by soft X-ray. The results were shown in Table 3. The ratio of the cortical width to the outer width was increased in the groups of Compound [IX] and Compound [X] by administration of 500 mg/kg for six weeks continuously; in particular, the significant effect was observed in the group of Compound [X], which indicated that the bone metabolic disorder induced by ovariectomy was improved.

TABLE 3

| Test compound | Outer width (mm) | Cortical width (mm) | Cortical/Outer |
|---|---|---|---|
| Nontreated | 1.75 ± 0.07 | 0.41 ± 0.11 | 0.233 ± 0.060 |
| OVX-control | 1.78 ± 0.10 | 0.34 ± 0.06 | 0.188 ± 0.025 |
| Compound [IX] 500 μg/kg | 1.65 ± 0.09 | 0.40 ± 0.06 | 0.245 ± 0.048 |
| Compound [X] 500 μg/kg | 1.68 ± 0.08 | 0.42 ± 0.08 | 0.250 ± 0.040* |

*p < 0.05% vs. OVX-control

At the same time, blood samples were collected from the animals administrated by 500mg/kg/day of Compound [IX] or Compound [X] for six weeks and checked several serum-biochemical parameters. Several tissues were also removed from these animals and observed macroscopically. No toxic sign was observed in these examinations.

What is claimed is:

1. A compound represented by the formula 1

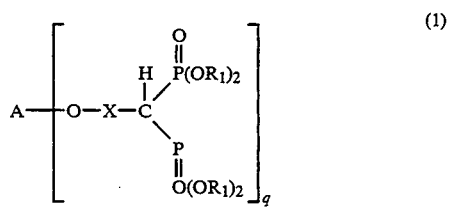

wherein

A-O denotes a residue of a compound selected from the group consisting of estrone, estradiol, estriol and their derivatives, which binds to a bisphosphonate group at the 3-position of a steroidal group, $R_1$ denotes H or a $C_1$-$C_6$ alkyl group, X denotes a single bond or a $C_1$-$C_{10}$-alkylene group, and q denotes 1, or a physiologically acceptable salt thereof.

2. A compound according to claim 1, wherein the compound is represented by the formula:

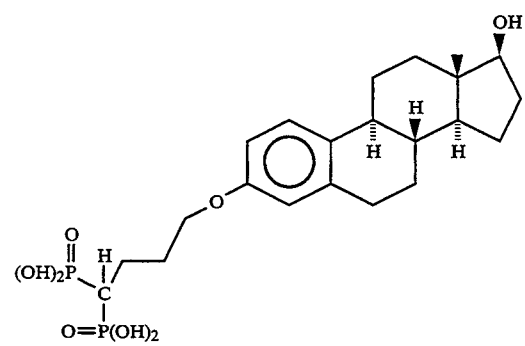

3. A compound according to claim 1, wherein the compound is represented by the formula:

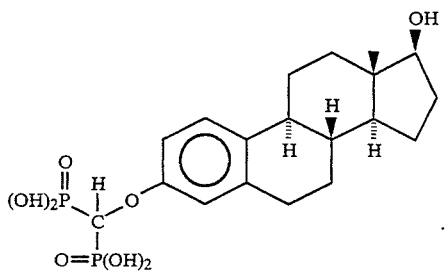

4. The compound according to claim 2 wherein X is a single bond.

5. The compound according to claim 2 wherein X is a $C_1$–$C_{10}$ alkylene group.

6. The compound according to claim 5 wherein the $C_1$–$C_{10}$ alkylene group is trimethylene group.

7. The compound according to claim 2 wherein A-O- is a residue of estra-1,3,5(10)-triene-3,17-diol and X is a single bond or a trimethylene group.

8. A pharmaceutical composition for treating bone diseases comprising an effective amount of the compound or physiologically acceptable salt thereof according to claim 2 in combination with a pharmaceutically acceptable carrier or excipient.

9. The pharmaceutical composition according to claim 8 wherein the bone disease is osteoporosis.

* * * * *